United States Patent
Park et al.

(10) Patent No.: US 7,816,673 B2
(45) Date of Patent: Oct. 19, 2010

(54) HETEROACENE COMPOUND, ORGANIC THIN FILM COMPRISING THE COMPOUND, AND ELECTRONIC DEVICE COMPRISING THE THIN FILM

(75) Inventors: Jong Il Park, Yongin-si (KR); Eun Jeong Jeong, Yongin-si (KR); Sang Yoon Lee, Yongin-si (KR); Bang Lin Lee, Yongin-si (KR); Kook Min Han, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 578 days.

(21) Appl. No.: 11/889,003

(22) Filed: Aug. 8, 2007

(65) Prior Publication Data

US 2008/0142792 A1 Jun. 19, 2008

(30) Foreign Application Priority Data

Dec. 13, 2006 (KR) ...................... 10-2006-0126931

(51) Int. Cl.
  *H01L 51/30* (2006.01)
  *C07D 307/00* (2006.01)
  *C07D 409/14* (2006.01)
  *C07D 487/22* (2006.01)
(52) U.S. Cl. ............ 257/40; 257/E51.029; 257/E51.05; 438/99; 548/417; 549/41; 549/456
(58) Field of Classification Search .................. 257/40, 257/E51.001–E51.052; 438/99; 548/416–417; 549/29, 41–43, 429, 456
See application file for complete search history.

(56) References Cited

U.S. PATENT DOCUMENTS 6,913,710 B2 7/2005 Farrand et al.
2003/0088112 A1* 5/2003 Holmes et al. ................ 549/41

OTHER PUBLICATIONS

Takiyama, K., et al. "2,7-Diphenyl[1]benzoselenopheno[3,2-b][1]benzoselenophene as a Stable Organic Semiconductor for a High-Performance Field-Effect Transistor." J. Am. Chem. Soc., vol. 128 (2006): pp. 3044-3050.*

Wex, B., et al. "New Organic Semiconductors and Their Device Performance as a Function of Thiophene Orientation." J. Mater. Chem., vol. 16 (2006): pp. 1121-1124.*

Laquindanum, J.G., et al. "Benzodithiophene Rings as Semiconductor Building Blocks." Adv. Mater., vol. 9 (1997): pp. 36-39.*

(Continued)

*Primary Examiner*—Matthew W Such
(74) *Attorney, Agent, or Firm*—Harness, Dickey & Pierce, P.L.C.

(57) ABSTRACT

A heteroacene compound includes a di-thieno-benzo-thieno-thiophene derivative, in which all six rings may be fused together, an organic thin film including the same, and an electronic device that includes the thin film as a carrier transport layer. The compound of example embodiments may have a compact planar structure to thus realize improved solvent solubility and processability. When the compound is applied to electronic devices, a deposition process or a room-temperature solution process may be applied, and as well, intermolecular packing and stacking may be efficiently realized, resulting in improved electrical properties, including increased charge mobility.

24 Claims, 1 Drawing Sheet

OTHER PUBLICATIONS

Xiao, K., et al. "A Highly pi-Stacked Organic Semiconductor for Field-Effect Transistors Based on Linearly Condensed Pentathienoacene." J. Am. Chem. Soc., vol. 127 (2005): pp. 13281-13286.*

Sirringhaus, H., et al. "Dibenzothienobisbenzothiophene—A Novel Fused-Ring Oligomer With High Field-Effect Mobility." J. Mater. Chem., vol. 9 (1999): pp. 2095-2101.*

Li, X.-C., et al. "A Highly pi-Stacked Organic Semiconductor for Thin Film Transistors Based on Fused Thiophenes." J. Am. Chem. Soc., vol. 120 (1998): pp. 2206-2207.*

Lance S. Fuller et al., "Thienothiphenes. Part 2. Synthesis, Metallation and Bromine Lithium Exchange Reactions of Thieno Thiophene and its Polybromo Derivatives", J. Chem. Soc., Perkin Transactions 1, 1997.

* cited by examiner

FIG. 1

HETEROACENE COMPOUND, ORGANIC THIN FILM COMPRISING THE COMPOUND, AND ELECTRONIC DEVICE COMPRISING THE THIN FILM

PRIORITY STATEMENT

This non-provisional application claims priority under U.S.C. §119 to Korean Patent Application No. 2006-126931, filed on Dec. 13, 2006, in the Korean Intellectual Property Office (KIPO), the entire contents of which are incorporated herein by reference.

BACKGROUND

1. Field

Example embodiments relate to a heteroacene compound and applications thereof. Other example embodiments relate to a heteroacene compound, in which all six rings may be fused together, an organic thin film comprising the compound, an electronic device comprising the thin film as a carrier transport layer and methods of fabricating the organic thin film and the electronic device.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may function as a conductive channel material for controlling the current between the source electrode and the drain electrode using the applied gate voltage.

As material for the channel layer of the TFT, organic materials, e.g., pentacene or polythiophene, have been studied. In the case of polymer or oligomer organic materials, e.g., F8T2, as polythiophene material, a solution process, e.g., spin casting, may be advantageously applied. However, problems of decreased charge mobility and increased off-state leakage current may be caused. Further, low-molecular-weight organic material, e.g., pentacene, may have increased charge mobility of about 3.2~5.0 cm²/Vs or more, but may require a relatively expensive apparatus for vacuum deposition at the time of forming a thin film. Therefore, the low-molecular-weight organic material may be unsuitable for use in the preparation of a film having a relatively large area, and processability may be undesirable.

Thus, there have been attempts to devise materials for channel layers having increased charge mobility and improved processability. The related art discloses dimeric bisbenzodithiophene, in which rings may be fused in groups of three and thus increased charge mobility may be realized. However, the development of material for a channel layer, satisfying improved electrical properties and processability, may be still required in the art.

SUMMARY

Accordingly, example embodiments have been made keeping in mind the above problems occurring in the related art, and example embodiments provide a low-molecular-weight heteroacene compound, which may have a compact planar structure in which all six rings may be fused together, thereby exhibiting increased charge mobility, and furthermore, enabling the use of a deposition process or a room-temperature solution process when applied to devices, therefore realizing improved processability.

Example embodiments provide a heteroacene compound, represented by Formula 1 below:

Formula 1 wherein $X_1$ and $X_2$ may be each independently O, S, Se, Te, or N—R, in which R may be selected from the group consisting of hydrogen, a $C_{1-12}$ alkyl group, a $C_{6-12}$ arylalkyl group, a $C_{6-12}$ aryl group, a $C_{1-12}$ alkoxy group, an acyl group, a sulfonyl group, and a carbamate group, and $R_1$, $R_2$, $R_3$, and $R_4$ may be each independently selected from the group consisting of hydrogen, a substituted or unsubstituted $C_{1-30}$ alkyl group, a substituted or unsubstituted $C_{1-30}$ alkenyl group, a substituted or unsubstituted $C_{1-30}$ alkynyl group, a substituted or unsubstituted $C_{1-30}$ heteroalkyl group, a substituted or unsubstituted $C_{6-30}$ arylalkyl group, a substituted or unsubstituted $C_{2-30}$ heteroarylalkyl group, a substituted or unsubstituted $C_{5-20}$ cycloalkyl group, a substituted or unsubstituted $C_{2-30}$ heterocycloalkyl group, a substituted or unsubstituted $C_{6-30}$ aryl group, and a substituted or unsubstituted $C_{2-30}$ heteroaryl group.

Example embodiments provide an organic thin film comprising the heteroacene compound. Example embodiments provide an electronic device comprising the organic thin film as a carrier transport layer.

Example embodiments provide a method of fabricating the organic thin film comprising dissolving one or more heteroacene compounds represented by Formula 1 above in an organic solvent to form a solution, and applying the solution to a substrate. Example embodiments also provide a method of fabricating an electronic device comprising forming the organic thin film according to example embodiments to perform as a carrier transport layer.

BRIEF DESCRIPTION OF THE DRAWING

Example embodiments will be more clearly understood from the following detailed description taken in conjunction with the accompanying drawings. FIG. 1 represents non-limiting, example embodiments as described herein.

It should be noted that this FIGURE is intended to illustrate the general characteristics of methods, structure and/or materials utilized in certain example embodiments and to supplement the written description provided below. This drawing is not, however, to scale and may not precisely reflect the precise structural or performance characteristics of any given embodiment, and should not be interpreted as defining or limiting the range of values or properties encompassed by example embodiments. In particular, the relative thicknesses and positioning of molecules, layers, regions and/or structural elements may be reduced or exaggerated for clarity. The use of similar or identical reference numbers in the drawing is intended to indicate the presence of a similar or identical element or feature.

DETAILED DESCRIPTION OF EXAMPLE EMBODIMENTS

Example embodiments will now be described in greater detail with reference to the accompanying drawings. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the FIGURES are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to example embodiments, the heteroacene compound is represented by Formula 1 below:

Formula 1 wherein $X_1$ and $X_2$ may be each independently O, S, Se, Te, or N—R, in which R may be selected from the group consisting of hydrogen, a $C_{1-12}$ alkyl group, a $C_{6-12}$ arylalkyl group, a $C_{6-12}$ aryl group, a $C_{1-12}$ alkoxy group, an acyl group, a sulfonyl group, and a carbamate group, and $R_1$, $R_2$, $R_3$, and $R_4$ may be each independently selected from the group consisting of hydrogen, a substituted or unsubstituted $C_{1-30}$ alkyl group, a substituted or unsubstituted $C_{1-30}$ alkenyl group, a substituted or unsubstituted $C_{1-30}$ alkynyl group, a substituted or unsubstituted $C_{1-30}$ heteroalkyl group, a substituted or unsubstituted $C_{6-30}$ arylalkyl group, a substituted or unsubstituted $C_{2-30}$ heteroarylalkyl group, a substituted or unsubstituted $C_{5-20}$ cycloalkyl group, a substituted or unsubstituted $C_{2-30}$ heterocycloalkyl group, a substituted or unsubstituted $C_{6-30}$ aryl group, and a substituted or unsubstituted $C_{2-30}$ heteroaryl group.

As represented by Formula 1, the heteroacene compound may have a structure in which all six aromatic or heteroaromatic rings may be fused together. Due to this compact planar molecular structure, when the compound is applied to actual devices, the oxidation potential may be uniform and stable, and furthermore, intermolecular packing and stacking may become more efficient, thus realizing increased charge mobility. Further, because the heteroacene compound is relatively easily synthesized, the heteroacene compound may be useful as semiconductor material or electron transport material. Furthermore, a substituent, e.g., an alkyl group, an alkenyl group, or an aryl group, may be introduced to heteroaromatic rings positioned at both terminal portions of the compound or a benzene ring positioned at the middle portion thereof, so that suitable solubility may be exhibited. Thus, in addition to the deposition process, the compound may be relatively simply applied through a room-temperature solution process, and may also be formed into a thin film having a relatively large area, resulting in effective processability and workability.

In Formula 1, the alkyl group may be a linear or branched type, examples thereof including methyl, ethyl, propyl, iso-butyl, sec-butyl, tert-butyl, pentyl, iso-amyl and/or hexyl. One or more hydrogen atoms included in the alkyl group may be substituted with a substituent. Such a substituent may be appropriately determined according to the choice of those skilled in the art, depending on the end use and need, examples of which may include, but may not be limited to, a $C_{1-10}$ alkyl group, a $C_{1-10}$ alkenyl group, a $C_{1-10}$ alkynyl group, a $C_{6-12}$ aryl group, a $C_{2-12}$ heteroaryl group, a $C_{6-12}$ arylalkyl group, a halogen atom, a cyano group, an amino group, an amidino group, a nitro group, an amide group, a carbonyl group, a hydroxyl group, a sulfonyl group, a carbamate group and/or a $C_{1-10}$ alkoxy group.

The alkenyl group or alkynyl group may have one or more carbon-carbon double bonds or triple bonds in the middle portion or the terminal portion of the alkyl group defined above. Specific examples thereof may include ethylene, propylene, butylene, hexylene and/or acetylene. One or more hydrogen atoms of the alkenyl group or alkynyl group may be substituted with the same substituent as in the alkyl group.

The heteroalkyl group refers to a radical formed as a result of replacing about one or more carbon atoms, for example, about 1~ about 5 carbon atoms, of the main chain of the alkyl group with a hetero atom, e.g., oxygen, sulfur, nitrogen, and phosphorus. About one or more hydrogen atoms of the heteroalkyl group may be substituted with the same substituent as in the alkyl group.

The cycloalkyl group refers to a monovalent monocyclic system having about 5~ about 30 carbon atoms, and the heterocycloalkyl group refers to an about 5- to about 30-membered monovalent monocyclic system having about 1, 2 or 3 hetero atoms selected from among N, O, P and S, with the remaining ring atoms being C. Further, about one or more hydrogen atoms of the cycloalkyl group or heterocycloalkyl group may be substituted with the same substituent as in the alkyl group.

The aryl group refers to an aromatic carbocyclic system having about one or more aromatic rings, the rings being attached or fused together through a pendent process. Specific examples of the aryl group may include aromatic groups, e.g., phenyl, naphthyl and/or tetrahydronaphthyl. Further, one or more hydrogen atoms of the aryl group may be substituted with the same substituent as in the alkyl group.

The arylalkyl group refers to a radical formed as a result of replacing some of the hydrogen atoms of the aryl group defined above with a lower alkyl radical, for example, methyl, ethyl and/or propyl, e.g., benzyl and phenylethyl. Further, one or more hydrogen atoms of the arylalkyl group may be substituted with the same substituent as in the alkyl group.

The heteroaryl group refers to an about 5- to about 30-membered aromatic ring system having about 1, 2 or 3 hetero atoms selected from among N, O, P and S, with the remaining ring atoms being C, the rings being attached or fused together through a pendent process. Further, one or more hydrogen atoms of the heteroaryl group may be substituted with the same substituent as in the alkyl group.

The heteroarylalkyl group refers to a radical formed as a result of replacing some of the hydrogen atoms of the heteroaryl group defined above with a lower alkyl radical, one or more hydrogen atoms of the heteroarylalkyl group being substituted with the same substituent as in the alkyl group.

The alkoxy group refers to radical-O-alkyl, in which the alkyl may be defined as above. Specific examples thereof may include methoxy, ethoxy, propoxy, iso-butyloxy, sec-butyloxy, pentyloxy, iso-amyloxy and/or hexyloxy. Further, one or more hydrogen atoms of the alkoxy group may be substituted with the same substituent as in the alkyl group.

For example, the heteroacene compound may be a dithienobenzothienothiophene derivative represented by Formula 2 below. $R_1$, $R_2$, $R_3$ and $R_4$ may be each independently hydrogen, a $C_{1-10}$ alkyl group, a $C_{1-10}$ alkenyl group, a $C_{6-12}$ arylalkyl group, or a $C_{6-12}$ aryl group, in the interest of solvent solubility and charge mobility.

Formula 2 wherein $R_1$, $R_2$, $R_3$ and $R_4$ may be defined as in Formula 1.

Examples of the compound of Formula 2 may include, but may not be limited to, compounds represented by Formulas 3 to 6 below:

Formula 3

Formula 4

-continued

5

Formula 5

Formula 6

The heteroacene compound of example embodiments may be formed using a conventional process of polymerizing aromatic or heteroaromatic compounds, for example, a chemical or electrochemical oxidation synthesis process and a condensation process using an organic transition metal compound, e.g., nickel or palladium. For example, according to the procedures of Reaction 1, 2 or 3, the compound may be synthesized, but example embodiments may not be limited thereto.

Reaction 1 in Reactions 1, 2 and 3, $X_1$, $X_2$, $R_1$, $R_2$, $R_3$ and $R_4$ may be defined as in Formula 1.

The above reactions may be conducted at a temperature ranging from about −78° C. to about room temperature in the air or in a nitrogen atmosphere using a heteroaromatic ring compound substituted with a halogen atom (for example, bromine) and/or lithium. As such, the solvent may be exemplified by toluene, dimethylformamide, N-methylpyrrolidinone, and tetrahydrofuran. A dehydrating catalyst may be an acidic catalyst, including Amberlyst 15.

The molecular weight of the heteroacene compound thus synthesized may be appropriately controlled depending on the end use and need, for example, may range from about 350 to about 3000.

In addition, example embodiments provide an organic thin film comprising the heteroacene compound, and an electronic device comprising the thin film.

The organic thin film, comprising the heteroacene compound mentioned above, may be used as a carrier transport layer, e.g., an organic semiconductor layer or a channel layer, of the electronic device. The electronic device comprising the thin film may exhibit increased processability and workability and improved electrical properties, including increased charge mobility.

The organic thin film may be formed by dissolving one or more heteroacene compounds in an organic solvent and applying the solution on a substrate through a conventional deposition process or a conventional room-temperature solution process. After the deposition or application, heat treatment may be performed, if necessary, thereby further increasing the density and uniformity of the thin film.

Specific examples of the organic solvent may include one or more typical organic solvents, for example, one or more selected from the group consisting of an aliphatic hydrocarbon solvent, e.g., hexane or heptane, an aromatic hydrocarbon solvent, e.g., toluene, pyridine, quinoline, anisol, mesitylene or xylene, a ketone-based solvent, e.g., methyl isobutyl ketone, 1-methyl-2-pyrrolidinone, cyclohexanone or acetone, an ether-based solvent, e.g., tetrahydrofuran or isopropyl ether, an acetate-based solvent, e.g., ethyl acetate, butyl acetate or propyleneglycol methyl ether acetate, an alcohol-based solvent, e.g., isopropyl alcohol or butyl alcohol, an amide-based solvent, e.g., dimethylacetamide or dimethylformamide, a silicon-based solvent, and mixtures thereof. The amount of the heteroacene compound that may be dissolved in the organic solvent may be appropriately determined according to the choice of those skilled in the art, and may range from about 0.01 wt % to about 50 wt % based on the total amount of the solution, in the interest of solubility and applicability.

Examples of the process of forming the organic thin film may include, but may not be limited to, thermal evaporation, vacuum deposition, laser deposition, screen printing, printing, imprinting, spin casting, dipping, ink jetting, roll coating, flow coating, drop casting, spray coating, or roll printing. The heat treatment process may be conducted at about 80° C.~ about 250° C. for a time period ranging from about 1 min to about 2 hours, but example embodiments may not be limited thereto.

The thickness of the organic thin film may be appropriately controlled, depending on the end use and need, in consideration of the type of compound and the type of solvent, and may range from about 200 Å to about 10,000 Å.

Examples of the electronic device comprising such an organic thin film as a carrier transport layer may include, but may not be limited to, TFTs, electroluminescent devices, photovoltaic devices, memory, and sensors. The organic thin film of example embodiments may be applied to the above devices using a typical process known in the art.

For example, the TFT may include a substrate, a gate electrode, a gate insulating layer, source/drain electrodes, and an organic semiconductor layer including the organic thin film of example embodiments.

The TFT of example embodiments may have a bottom contact structure comprising a substrate, a gate electrode formed on the substrate, a gate insulating layer formed on the gate electrode, source/drain electrodes formed on the gate insulating layer, and a semiconductor layer formed on the gate insulating layer and the source/drain electrodes, a top contact structure comprising a substrate, a gate electrode formed on the substrate, a gate insulating layer formed on the gate electrode, a semiconductor layer formed on the gate insulating layer, and source/drain electrodes formed on the semiconductor layer, and a top gate structure comprising a substrate, source/drain electrodes formed on the substrate, a semiconductor layer formed on the substrate and the source/drain electrodes, a gate insulating layer formed on the semiconductor layer, and a gate electrode formed on the gate insulating layer. However, example embodiments may not be limited thereto, and the structure may be modified within a range that does not inhibit the purpose of example embodiments.

The substrate may not be particularly limited as long as it does not inhibit the purpose of example embodiments, and examples thereof may include, but may not be limited to, silica, glass, and plastic, which may be appropriately used according to the choice of those skilled in the art, depending on the end use. Further, examples of the plastic substrate may include, but may not be limited to, polyethylene naphthalate, polyethylene terephthalate, polycarbonate, polyvinylbutyral, polyacrylate, polyimide, polynorbornene, and polyethersulfone.

For the gate electrode and the source/drain electrodes, conventional materials may be used without limitation, for example, one or more selected from among metals, e.g., gold (Au), silver (Ag), aluminum (Al), nickel (Ni), molybdenum (Mo), tungsten (W), and chromium (Cr), alloys thereof (e.g., molybdenum/tungsten (Mo/W) alloy), metal oxides, e.g., indium tin oxide (ITO) and indium zinc oxide (IZO), and conductive polymers, e.g., polythiophene, polyaniline, polyacetylene, polypyrrole, polyphenylene vinylene, and a mixture of PEDOT (polyethylenedioxythiophene) and PSS (polystyrenesulfonate). The gate electrode may be about 500 Å~ about 2,000 Å thick and the source/drain electrodes may be about 500 Å~ about 2,000 Å thick. Further, these electrodes may be formed through a patterning process depending on the end use and need.

The gate insulating layer may be an insulating material having a high dielectric constant. Specific examples thereof may include, but may not be limited to, a ferroelectric insulator, selected from among $Ba_{0.33}Sr_{0.66}TiO_3$ (BST), $Al_2O_3$, $Ta_2O_5$, $La_2O_5$, $Y_2O_5$, and $TiO_2$, an inorganic insulator selected from among $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $Bi_4Ti_3O_{12}$, $SiO_2$, $SiN_x$, and AlON, and an organic insulator, including polyimide, benzocyclobutene (BCB), parylene, polyacrylate, polyvinylalcohol and polyvinylphenol. Such a gate insulating layer may be about 1,000 Å~ about 10,000 Å thick, but example embodiments may not be limited thereto. This layer may be formed through a patterning process depending on the end use and need.

A better understanding of example embodiments may be obtained in light of the following synthesis examples and examples, which are set forth to illustrate, but are not to be construed as limiting example embodiments.

Preparation of Heteroacene Compound

Preparative Example 1

(1) Synthesis of Compound 2

Thienothiophene 1 could be synthesized using a process developed by Iddon et al (Lance S. Fuller, Brian Iddon, Kevin A. Smith *J. Chem. Soc., Perkin Trans.* 1, 1997, 3465-3470). The thienothiophene (about 3.35 g, about 24 mmol) was dissolved in about 50 ml of dry ether, and the solution was added in droplets to about 100 ml of a dry ether solution containing butyl lithium (about 21 ml of about 2.5 M in a hexane solution) cooled to about 0° C., after which the temperature was gradually increased and a stirring process was performed at about room temperature for about 2 hours. To the turbid solution, dimethylformamide (DMF, about 4.6 ml) was slowly added in droplets and then the mixture was stirred overnight. About 50 ml of a saturated solution of ammonium chloride was added thereto, and a precipitate was filtered and then washed several times with water and ether, thus obtaining a desired compound 2 (yield about 75%).

$^1$NMR (CDCl$_3$) d 10.1 (s, 2H), 8.05 (s, 2H).

(2) Synthesis of Compound 3

2,3-Dibromothiophene (about 2.42 g, about 10 mmol) was dissolved in about 100 ml of an about 5:1 solution of ether and THF and then cooled to about −78° C. Butyl lithium (11 mmol) was slowly added in droplets thereto and then the mixture was stirred for about 30 min. The solution was slowly added in droplets to the solution (about −78° C.) of the compound 2 (about 0.99 g, about 5 mmol) in about 100 ml of THF and stirred, and the temperature was gradually increased to about room temperature. About 100 ml of a saturated solution of ammonium chloride was added thereto and thus the reaction was terminated. Thereafter, about 200 ml of ether was added and the organic layer was separated. The separated organic layer was washed with brine, dried over MgSO$_4$ and then concentrated, thus obtaining yellow oil, which was then purified through silica chromatography (hexane:ethylacetate=about 5:1), thereby yielding a desired diol compound.

$^1$NMR (CDCl$_3$) d 7.32 (d, 2H), 7.18 (s, 2H), 6.97 (dd, 2H), 6.42 (d, 2H), 2.76 (d, 2H).

The diol compound (about 1.4 g, about 2.7 mmol) was dissolved in about 150 ml of dichloromethane, and ZnI$_2$ (about 2.75 g, about 8.6 mmol) and NaCNBH$_3$ (about 2.4 g, about 37.66 mmol) were slowly added thereto. The mixture was stirred at about room temperature for about 24 hours, and then passed through a celite pad. The filtrate was washed with a saturation solution of ammonium chloride and water, dried over MgSO$_4$ and then concentrated under reduced pressure, thus obtaining yellow oil. This oil was purified through silica chromatography, giving a desired compound 3 (yield about 80%).

$^1$NMR (CDCl$_3$) d 7.17 (d, 2H), 6.98 (s, 2H), 6.94 (d, 2H), 4.34 (s, 4H)

(3) Synthesis of Compound 4

To a solution of butyl lithium (about 1.73 mmol) in THF (about 10 ml), cooled to about −78° C., a solution of the compound 4 (about 385 mg, about 0.79 mmol) in THF (about 5 ml) was slowly added in droplets. The solution was stirred at about −78° C. for about 20 min, added with DMF (about 150 ml, about 1.97 mmol), and further stirred for about 2 hours. Water was poured in to thus terminate the reaction, after which about 30 ml of ether was added and a washing process was performed using water and brine. Then, the organic layer was dried over MgSO$_4$ and concentrated under reduced pressure to thus prepare colorless oil, which was then purified through silica chromatography, thus obtaining a compound 4 (yield about 70%).

NMR (CDCl$_3$) d 10.1 (s, 2H), 7.43 (d, 2H), 7.20 (d, 2H), 7.02 (s, 2H), 4.76 (s, 4H).

(4) Synthesis of Compound 5

Figure 1:
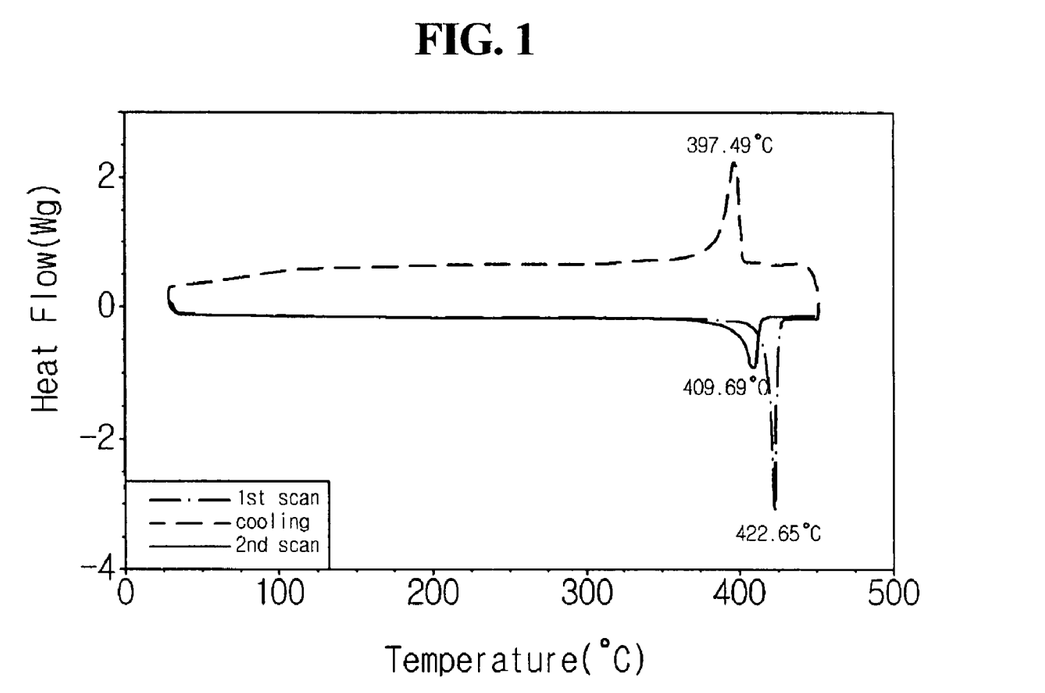
FIG. 1 is a graph illustrating the result of differential scanning calorimetry (DSC) of the heteroacene compound synthesized in Preparative Example 1 of example embodiments.

The compound 4 (about 200 mg) was dissolved in about 10 ml of toluene, and Amberlyst 15 was added (about 300 mg), after which the mixture was stirred for reflux while water was removed using a Dean-Stark trap. After about 24 hours, a beige solid was precipitated. The temperature was decreased to about room temperature, and Amberlyst 15 was precipitated. The supernatant was filtered off, thus obtaining a desired compound 5 as a yellow solid (a fluorescent sky-blue color) (yield about 60%). The compound 5 was purified in an increased vacuum (about <10$^{-4}$ torr) through sublimation (m.p. about 423° C.), and evaluated using DSC (Differential Scanning Calorimetry). The results are shown in FIG. 1; GC-MS (M+) 352.

Preparative Example 2

Reaction 5

(1) Synthesis of Compound 7

Tetrabromo-thieno[3,2-b]thiophene (about 1.2 g, about 2.7 mmol) was dissolved in anhydrous THF and cooled to about −78° C. in a nitrogen atmosphere. About 2.5 M of butyl lithium (about 2.5 ml, about 6.25 mmol) was slowly added thereto, and the mixture was stirred for about 30 min. Thereafter, a solution of 2-octyl-5-formyl thiophene (about 1.3 g, about 5.4 mmol) in about 30 ml of THF was slowly added in droplets to the reaction mixture. The reaction temperature was gradually increased to about room temperature, and a stirring process was performed at about room temperature for about 3 hours, after which a saturated solution of $NH_4Cl$ was poured in to thus terminate the reaction. The reaction solution was diluted with ether, and the separated organic layer was washed with water and brine. The organic solution was dried over anhydrous $MgSO_4$, filtered, and concentrated under reduced pressure, thus obtaining a pale yellow solid. The solid was recrystallized using ethyl acetate, thereby obtaining a white diol solid (about 1.8 g, about 2.42 mmol).

NMR ($CDCl_3$) d 6.90 (d, 2H), 6.65 (d, 2H), 6.35 (d, 2H), 2.80 (t, 4H), 2.60 (d, 2H), 1.65 (m, 4H), 1.30 (m, 20H), 0.90 (t, 6H).

The solid thus obtained was dissolved in methylene chloride, and $ZnI_2$ (about 2.5 g, about 7.74 mmol) and $NaCNBH_3$ (about 2.2 g, about 34 mol) were sequentially added thereto, and the mixture was stirred at about room temperature for about 24 hours. The stirred solution was passed through a celite pad to thus filter a white solid, after which the filtrate was washed with about 1N HCl, water, and brine, dried and concentrated, thus obtaining a pale yellow solid. The solid was titrated using ether, thereby yielding a white solid compound 7 (about 1.3 g, about 1.83 mmol).

NMR ($CDCl_3$) d 6.75 (d, 2H), 6.60 (d, 2H), 4.30 (s, 4H), 2.75 (t, 4H), 1.65 (m, 4H), 1.30 (m, 20H), 0.90 (t, 6H).

(2) Synthesis of Compound 8

The compound 7 (about 620 mg, about 0.87 mmol) was dissolved in anhydrous THF and cooled to about −78° C. in a nitrogen atmosphere. About 2.5 M butyl lithium (about 800 ml, about 2.0 mmol) was slowly added in droplets thereto, and the mixture was stirred for about 30 min. Thereafter, DMF (about 160 ml, about 2.0 mmol) was slowly added in droplets thereto, the reaction temperature was gradually increased to about room temperature, and a stirring process was performed at about room temperature for about 3 hours. The stirred solution was diluted with ether, and washed with a saturation solution of $NH_4Cl$, water and brine. The concentrated brown solid was purified through column chromatography (Hex:EA=about 10:1), thus obtaining a desired white solid (about 410 mg, about 0.65 mmol).

NMR ($CDCl_3$) d 10.2 (s, 2H), 6.75 (d, 2H), 6.60 (d, 2H), 4.75 (s, 4H), 2.75 (t, 4H), 1.65 (m, 4H), 1.30 (m, 20H), 0.90 (t, 6H).

(3) Synthesis of Compound 9

The compound 8 was subjected to the same synthesis process as the process of synthesizing the compound 5 in Preparative Example 1, thus obtaining a desired compound 9 as a white solid.

NMR ($C_6D_5CD_3$) d 7.80 (d, 2H), 7.45 (s, 4H), 2.75 (t, 4H), 1.65 (m, 4H), 1.30 (m, 20H), 0.90 (t, 6H); m.p.>300° C.; GC-MS (M+) 575.

Preparative Example 2

The desired compound 12 was synthesized in the same manner as in Preparative Example 2, with the exception that 2-heptylcarbonylthiophene was used instead of 2-octyl-5-formyl thiophene.

NMR (CDCl$_3$) 7.75 (d, 2H), 7.57 (d, 2H), 7.43 (s, 2H), 2.70 (t, 4H), 1.75 (m, 4H), 1.60 (m, 4H), 1.34 (m, 8H), 0.95 (t, 6H); GC-MS (M+) 547.

Preparative Example 4

The desired compound 15 was synthesized in the same manner as in Preparative Example 3, with the exception that 3-heptylcarbonylthiophene was used instead of 2-heptylcarbonylthiophene.

NMR (CDCl$_3$) 7.80 (d, 2H), 7.60 (d, 2H), 7.49 (s, 2H) 2.68 (t, 4H), 1.74 (m, 4H), 1.58 (m, 4H), 1.32 (m, 8H), 0.90 (t, 6H); GC-MS (M+) 547.

Fabrication of Organic Thin Film Transistor

Example 1

On a washed glass substrate, aluminum (Al) for a gate electrode was deposited to a thickness of about 1000 Å through sputtering, and then organic and inorganic hybrid insulating material was applied through spin casting and dried at about 200° C. for about 2 hours, thus forming a gate insulating layer about 7000 Å thick. Subsequently, gold (Au) for source/drain electrodes was deposited thereon to a thickness of about 700 Å through thermal evaporation. Thereafter, the compound synthesized in Preparative Example 1 was deposited to a thickness of about 700 Å through thermal evaporation to thus prepare an organic semiconductor layer, thereby fabricating an organic thin film transistor (OTFT).

Example 2

An OTFT was fabricated in the same manner as in Example 1, with the exception that the solution (about 30 mg/ml) of the compound of Preparative Example 4 in chlorobenzene was subjected to spin casting at about 1000 rpm to thus form the organic semiconductor layer about 700 Å thick.

Comparative Example 1

An OTFT was fabricated in the same manner as in Example 1, with the exception that bisbenzodithiophene, represented by Formula 7, below, was used, instead of the compound of Preparative Example 1.

Formula 7

[Evaluation of Properties of OTFT]

The charge mobility of the OTFTs fabricated in Examples 1 and 2 and Comparative Example 1 was measured as follows. The results are shown in Table 1 below.

The charge mobility was calculated from the following current equation for the saturation region using the current transfer curve. For example, the current equation for the saturation region was converted into a graph relating $(I_{SD})^{1/2}$ and $V_G$, and the charge mobility was calculated from the slope of the converted graph:

$$I_{SD} = \frac{WC_0}{2L}\mu(V_G - V_T)^2$$

$$\sqrt{I_{SD}} = \sqrt{\frac{\mu C_0 W}{2L}} (V_G - V_T)$$

$$\text{slope} = \sqrt{\frac{\mu C_0 W}{2L}}$$

$$\mu_{FET} = (\text{slope})^2 \frac{2L}{C_0 W}$$

wherein $I_{SD}$ is source-drain current, $\mu$ or $\mu_{FET}$ is charge mobility, $C_o$ is oxide film capacitance, W is the channel width, L is the channel length, $V_G$ is the gate voltage, and $V_T$ is the threshold voltage.

TABLE 1

|         | Charge Mobility (cm$^2$/Vs) |
|---------|------------------------------|
| Ex. 1   | 0.08                         |
| Ex. 2   | 0.03                         |
| C. Ex. 1| 0.02                         |

As is apparent from Table 1, the OTFTs using the heteroacene compounds of example embodiments may have improved charge mobility.

As described hereinbefore, example embodiments provide a heteroacene compound, an organic thin film comprising the compound, and an electronic device comprising the thin film. According to example embodiments, the heteroacene compound may have a compact planar structure in which all six rings may be fused together, thus exhibiting improved solubility and processability. When the compound of example embodiments is applied to electronic devices, a conventional deposition process or a room-temperature solution process may be conducted, and intermolecular packing and stacking may also be efficiently realized, resulting in improved electrical properties, including increased charge mobility.

Although example embodiments have been disclosed for illustrative purposes, those skilled in the art will appreciate that various modifications, additions and substitutions are possible, without departing from the scope and spirit of the accompanying claims.

What is claimed is:

1. A heteroacene compound, which is represented by Formula 1 below:

Formula 1 wherein $X_1$ and $X_2$ are each independently O, S, Se, Te, or N—R, in which R is selected from the group consisting of hydrogen, a $C_{1-12}$ alkyl group, a $C_{6-12}$ arylalkyl group, a $C_{6-12}$ aryl group, a $C_{1-12}$ alkoxy group, an acyl group, a sulfonyl group, and a carbamate group, and $R_1$, $R_2$, $R_3$, and $R_4$ are each independently selected from the group consisting of hydrogen, a substituted or unsubstituted $C_{1-30}$ alkyl group, a substituted or unsubstituted $C_{1-30}$ alkenyl group, a substituted or unsubstituted $C_{1-30}$ alkynyl group, a substituted or unsubstituted $C_{1-30}$ heteroalkyl group, a substituted or unsubstituted $C_{6-30}$ arylalkyl group, a substituted or unsubstituted $C_{2-30}$ heteroarylalkyl group, a substituted or unsubstituted $C_{5-20}$ cycloalkyl group, a substituted or unsubstituted $C_{2-30}$ heterocycloalkyl group, a substituted or unsubstituted $C_{6-30}$ aryl group, and a substituted or unsubstituted $C_{2-30}$ heteroaryl group.

2. The heteroacene compound as set forth in claim 1, wherein a substituent, which is substituted in the alkyl group, the alkenyl group, the alkynyl group, the heteroalkyl group, the arylalkyl group, the heteroarylalkyl group, the cycloalkyl group, the heterocycloalkyl group, the aryl group, and the heteroaryl group, is one or more selected from the group consisting of a $C_{1-10}$ alkyl group, a $C_{1-10}$ alkenyl group, a $C_{1-10}$ alkynyl group, a $C_{6-12}$ aryl group, a $C_{2-12}$ heteroaryl group, a $C_{6-12}$ arylalkyl group, a halogen atom, a cyano group, an amino group, an amidino group, a nitro group, an amide group, a carbonyl group, a hydroxyl group, a sulfonyl group, a carbamate group, and a $C_{1-10}$ alkoxy group.

3. The heteroacene compound as set forth in claim 1, wherein the heteroacene compound is a dithienobenzothienothiophene derivative represented by Formula 2 below:

Formula 2 wherein $R_1$, $R_2$, $R_3$ and $R_4$ are defined as in Formula 1.

4. The heteroacene compound as set forth in claim 3, wherein the $R_1$, $R_2$, $R_3$ and $R_4$ are each independently hydrogen, a $C_{1-10}$ alkyl group, a $C_{1-10}$ alkenyl group, a $C_{6-12}$ arylalkyl group, or a $C_{6-12}$ aryl group.

5. The heteroacene compound as set forth in claim 3, wherein the dithienobenzothienothiophene derivative of Formula 2 is represented by Formulas 3 to 6 below:

Formula 3

Formula 4

Formula 5

Formula 6

6. The heteroacene compound as set forth in claim 1, wherein the heteroacene compound has an average molecular weight ranging from about 350 to about 3000.

7. An organic thin film, comprising the heteroacene compound of claim 1.

8. The organic thin film as set forth in claim 7, wherein the organic thin film is formed through thermal evaporation, vacuum deposition, laser deposition, screen printing, printing, imprinting, spin casting, dipping, ink jetting, roll coating, flow coating, drop casting, spray coating, or roll printing.

9. The organic thin film as set forth in claim 7, wherein the thickness of the organic thin film ranges from about 200 Å to about 10,000 Å.

10. An electronic device, comprising the organic thin film of claim 7 as a carrier transport layer.

11. The electronic device as set forth in claim 10, wherein the electronic device is a thin film transistor, an electroluminescent device, a photovoltaic device, memory, or a sensor.

12. The electronic device as set forth in claim 11, wherein the thin film transistor includes a substrate, a gate electrode, a gate insulating layer, source/drain electrodes, and an organic semiconductor layer including the organic thin film.

13. The electronic device as set forth in claim 12, wherein the thin film transistor has a bottom contact, top contact or top gate structure.

14. The electronic device as set forth in claim 12, wherein the substrate is made of silica, glass, and plastic.

15. The electronic device as set forth in claim 12, wherein the gate electrode and the source/drain electrodes are made of one or more of metals, alloys thereof, and conductive polymers.

16. The electronic device as set forth in claim 12, wherein the thickness of the gate electrode and the source drain electrodes ranges from about 500 Å~ about 2,000 Å.

17. The electronic device as set forth in claim 12, wherein the gate insulating layer is made of an insulating material having a high dielectric constant.

18. The electronic device as set forth in claim 12, wherein the thickness of the gate insulating layer ranges from about 1,000 Å~ about 10,000 Å thick.

19. A method of fabricating an organic thin film, comprising:
dissolving one or more heteroacene compounds represented by Formula 1 below:

Formula 1 wherein $X_1$ and $X_2$ are each independently O, S, Se, Te, or N—R, in which R is selected from the group consisting of hydrogen, a $C_{1-12}$ alkyl group, a $C_{6-12}$ arylalkyl group, a $C_{6-12}$ aryl group, a $C_{1-12}$ alkoxy group, an acyl group, a sulfonyl group, and a carbamate group, and $R_1$, $R_2$, $R_3$, and $R_4$ are each independently selected from the group consisting of hydrogen, a substituted or unsubstituted $C_{1-30}$ alkyl group, a substituted or unsubstituted $C_{1-30}$ alkenyl group, a substituted or unsubstituted $C_{1-30}$ alkynyl group, a substituted or unsubstituted $C_{1-30}$ heteroalkyl group, a substituted or unsubstituted $C_{6-30}$ arylalkyl group, a substituted or unsubstituted $C_{2-30}$ heteroarylalkyl group, a substituted or unsubstituted $C_{5-20}$ cycloalkyl group, a substituted or unsubstituted $C_{2-30}$ heterocycloalkyl group, a substituted or unsubstituted $C_{6-30}$ aryl group, and a substituted or unsubstituted $C_{2-30}$ heteroaryl group, in an organic solvent to form a solution; and applying the solution to a substrate.

20. The method of claim 19, wherein the organic solvent is selected from the group consisting of an aliphatic hydrocarbon solvent, an aromatic hydrocarbon solvent, a ketone-based solvent, an ether-based solvent, an acetate-based solvent, an alcohol-based solvent, an amide-based solvent, a silicon-based solvent, and mixtures thereof.

21. The method of claim 19, wherein the amount of the heteroacene compound dissolved in the organic solvent ranges from about 0.01 wt % to about 50 wt % based on the total amount of the solution.

22. The method of claim 19, further comprising:
performing a heat treatment process on the organic thin film.

23. The method of claim 22, wherein the heat treatment process is performed at about 80° C.~ about 250° C. for a time period ranging from about 1 min to about 2 hours.

24. A method of fabricating an electronic device comprising forming the organic thin film according to claim 19 to perform as a carrier transport layer.

* * * * *